United States Patent
Morrow et al.

(10) Patent No.: US 7,303,612 B2
(45) Date of Patent: Dec. 4, 2007

(54) UV REFLECTIVE CAVITY AND METHOD OF PROVIDING SAME

(75) Inventors: William H. Morrow, Barrie (CA); Larry James McLean, Barrie (CA); John Van Adrichem, Barrie (CA)

(73) Assignee: L2B Environmental Systems Inc., Barrie, Ontario (CA)

( * ) Notice: Subject to any disclaimer, the term of this patent is extended or adjusted under 35 U.S.C. 154(b) by 314 days.

(21) Appl. No.: 11/089,242

(22) Filed: Mar. 24, 2005

(65) Prior Publication Data

US 2006/0215257 A1 Sep. 28, 2006

(51) Int. Cl.
*G02B 13/14* (2006.01)
(52) U.S. Cl. ..................... 96/224; 250/432 R; 359/359
(58) Field of Classification Search ............... 96/224; 210/198.1, 205, 748; 422/24, 186.3; 250/432 R, 250/435–438; 359/359, 360, 850
See application file for complete search history.

(56) References Cited

U.S. PATENT DOCUMENTS

| | | | | | |
|---|---|---|---|---|---|
| 4,766,321 | A | * | 8/1988 | Lew et al. | 250/431 |
| 4,877,964 | A | * | 10/1989 | Tanaka et al. | 250/455.11 |
| 5,037,618 | A | * | 8/1991 | Hager | 422/186.03 |
| 5,523,057 | A | * | 6/1996 | Mazzilli | 422/121 |
| 5,656,242 | A | * | 8/1997 | Morrow et al. | 96/224 |
| 5,879,435 | A | * | 3/1999 | Satyapal et al. | 96/16 |
| 6,221,314 | B1 | * | 4/2001 | Bigelow | 422/24 |
| 6,500,387 | B1 | * | 12/2002 | Bigelow | 422/24 |
| 6,589,489 | B2 | | 7/2003 | Morrow et al. | |
| 2003/0058555 | A1 | * | 3/2003 | Takino | 359/850 |
| 2003/0059549 | A1 | | 3/2003 | Morrow et al. | |
| 2003/0131734 | A1 | * | 7/2003 | Engel et al. | 96/224 |
| 2004/0021090 | A1 | * | 2/2004 | Cekic et al. | 250/435 |

* cited by examiner

Primary Examiner—Frank M. Lawrence
(74) Attorney, Agent, or Firm—Ladas & Parry LLP

(57) ABSTRACT

A UV reflective cavity may be provided in a duct by attaching a plurality of tiles to the interior surface of the duct, each of the tiles having UV reflective surface.

15 Claims, 3 Drawing Sheets

UV REFLECTIVE CAVITY AND METHOD OF PROVIDING SAME

FIELD OF THE INVENTION

The present invention relates to ultra-violet light (UV) reflective cavities and methods of providing same.

BACKGROUND OF THE INVENTION

Often Ultra-Violet (UV) light is used to remove unwanted organic material, such as viruses, bacteria and other bio-organisms from the air or water. In the applicant's U.S. Pat. No. 6,589,489 issued Jul. 8, 2003 (the contents of which are hereby incorporated herein by reference), an air purifier is described that uses UV light. Contaminated air enters such a device and is subject to UV light from one or more lamp sources. The air that leaves such a device is significantly reduced in unwanted organic material.

To increase efficiency, the UV produced by the sources within the air purifier is preferably not absorbed by the inner surfaces but, rather, is reflected. Often inner surfaces of such air purifiers are made of aluminum to provide a suitable amount of UV reflection. In a more sophisticated approach, these inner surfaces may be provided with a self-cleaning UV reflective coating, such as a coating described in applicant's previously filed U.S. Patent publication no. 20030059549 published Mar. 27, 2003 (the contents of which are hereby incorporated herein by reference).

Where the UV reflective surfaces are compromised in some manner, it may become necessary to remove and refurbish, or simply replace, the air purifier. This could be an expensive venture. Where it is desired to purify air passing through existing ducting, it may be necessary to divert the air through a suitably constructed air purifier. However, such a solution can be awkward to implement and can increase the resistance to air flow through the duct work. Therefore, there is a need for an approach to purifying air that may ameliorate these problems.

SUMMARY OF THE INVENTION

A UV reflective cavity may be provided in a duct by attaching a plurality of tiles to the interior surface of the duct, each of the tiles having UV reflective surface.

In accordance with an aspect of the present invention there is provided a method of providing a UV reflective cavity, comprising: in a duct having a source of UV light, attaching a plurality of tiles, each having a UV reflective surface, to the interior surface of said duct.

In accordance with another aspect of the present invention there is provided a method of constructing an air purifier comprising: attaching a plurality of tiles, each with a UV reflective surface, to an interior surface of an air duct; and providing a source of UV light for illuminating said plurality of tiles.

In accordance with a further aspect of the present invention there is provided an air purifier, comprising: an air duct; a plurality of tiles, each of said tiles having a UV reflective surface, adhered to the interior surface of said duct; a source of UV light for illuminating said tiles.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures which illustrate example embodiments of this invention.

DETAILED DESCRIPTION

Figure 1:
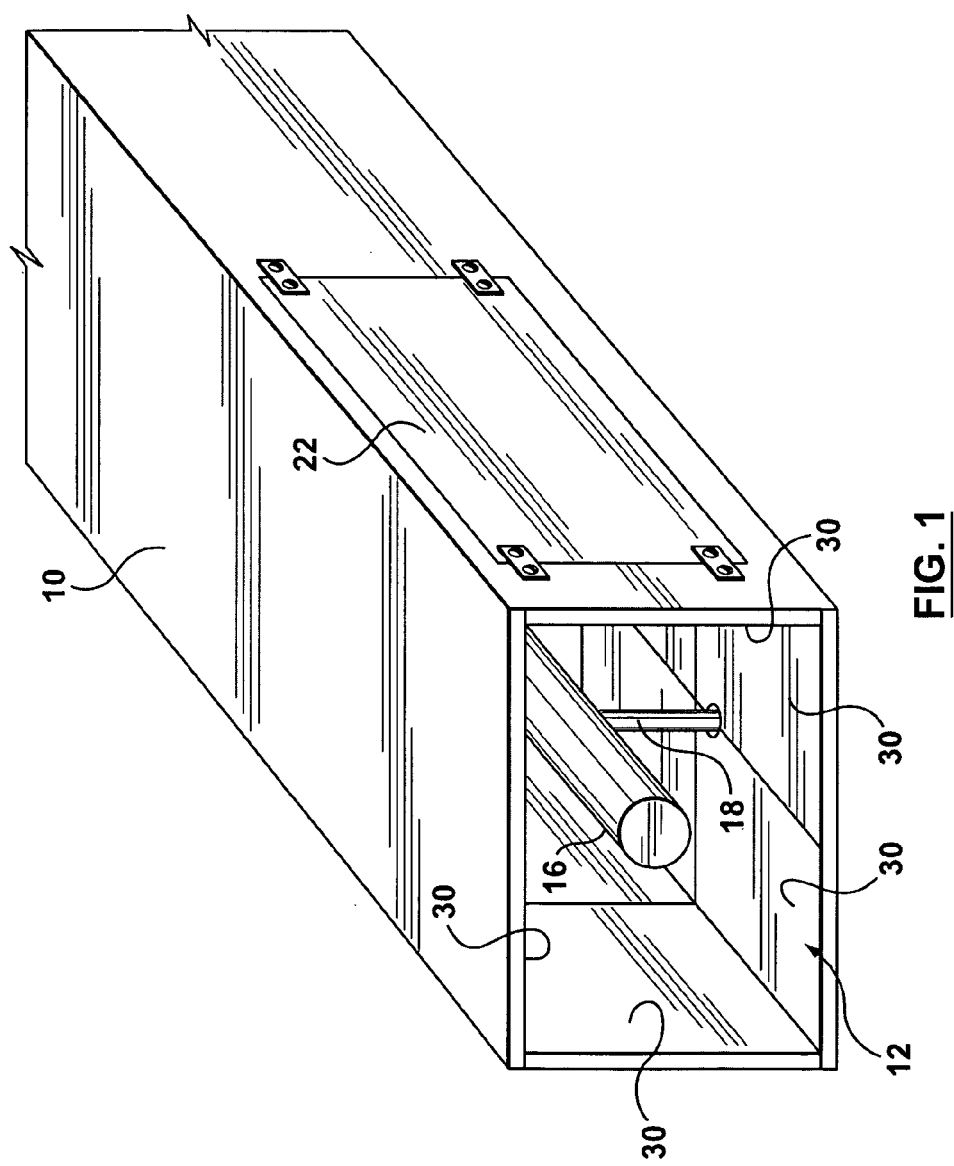
FIG. 1 is a perspective view of a duct having an air purifier made in accordance with this invention.
Figure 2:
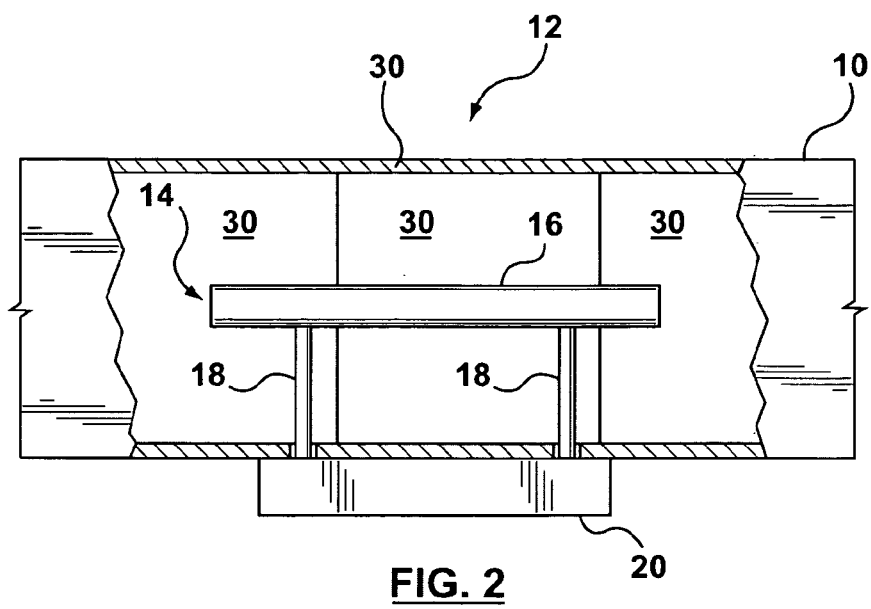
FIG. 2 is a cut-away side view of the duct of FIG. 1.

Turning to FIGS. 1 and 2, an air duct 10 has an air purifier 12 associated therewith. The air purifier 12 has a source 14 of UV light. The light source 14 may be a UV emitting tube 16 supported within duct 10 on supports 18. A ballast 20 for the tube may be attached to the outside of the duct 10. At least one of the supports 18 may be an electrical conduit through which electrical wiring runs from the ballast 20 to the tube 16 in order to provide current to the tube.

Figure 3:
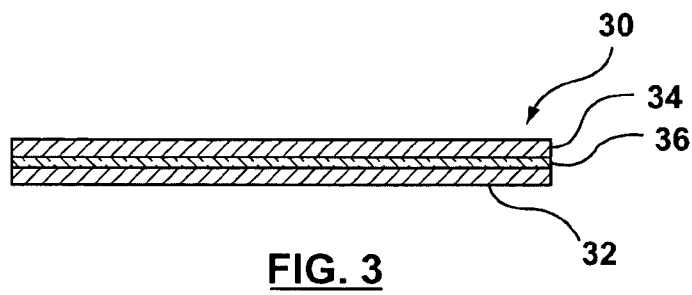
FIG. 3 is an enlarged cross-sectional view of a tile for use in the duct of FIG. 1 made in accordance with one aspect of the present invention.
Figure 4:
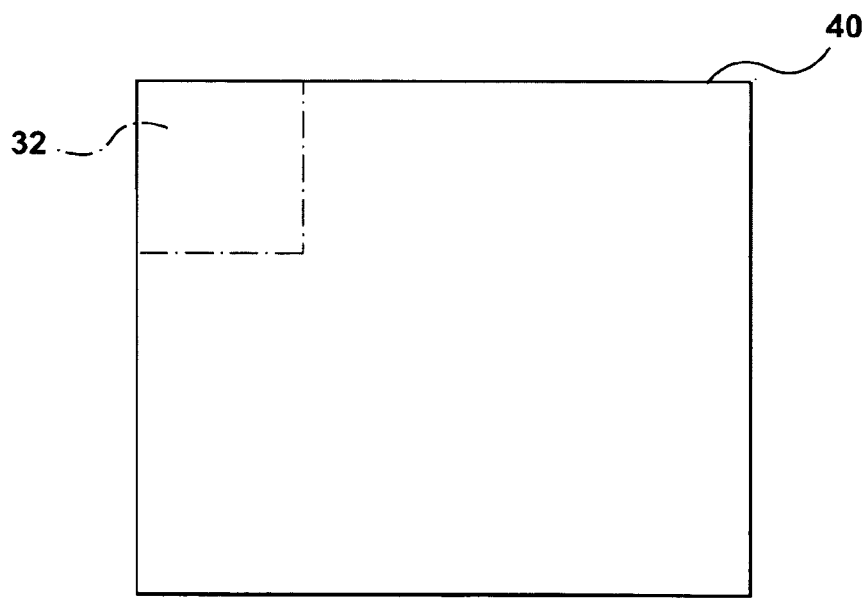
FIG. 4 is a schematic view of a large sheet from which tiles for use in the duct of FIG. 1 may be cut.

A plurality of tiles 30 are attached to the inner surface of the duct 10. Assuming that the duct 10 is made of a magnetic material (i.e., a material which will be attracted by a magnet), such as sheet steel, the tiles 30 may be as illustrated in FIG. 3. Turning to FIG. 3, a tile 30 has a basal lamina 32 which is a flexible ferromagnetic sheet. For example, lamina 32 may be a rubber sheet or flexible polymer (such as polyethylene) impregnated with ferromagnetic particles. A flexible UV reflective lamina 34, such as an aluminum foil sheet, is adhered to the ferromagnetic sheet by a layer 36 of adhesive. Turning to FIG. 4, the tiles 30 may be cut to any desired size and shape from a large sheet 40.

The air purifier 10 may be installed in an existing duct as follows. First, to gain access to the interior of the duct, either a removable panel 22 (FIG. 1) may be removed, or a panel may be cut out of the duct. Holes may be drilled to accommodate tube 16 supporting posts 18 and the posts may be inserted through the holes. The wiring in the posts may then be connected to the ballast 20 and the supports mounted to the ballast. The ballast itself may then be attached to the outside of the duct using, for example, screws. At this stage, the source 14 of UV light is now mounted within the duct 10. Next tiles 30 may be attached to the interior surface of the duct around the UV source 14 by simply placing the ferromagnetic lamina 32 of each tile against the inner surface of the duct. In this regard, the tiles may be cut down in size as required to allow the tiles to fit properly. For example, a corner (or side) of a tile that abuts a support 18 may be trimmed back. (Installation may be made easier by providing tiles that end at the supports, otherwise, it is necessary to slit a tile to allow its installation around a support post.) The tiles may arrive on the job site pre-cut to a standard size, or sizes. Alternatively, the tiles may be cut on site to the required sizes (and shapes) from a larger sheet 40. Tiles may also be installed on the panel removed from the duct. Once the tiles have been installed, the panel may be re-installed on the duct and the ballast wired to a source of electricity.

After installation, the light source 14 may be illuminated to provide UV light within the duct 10 at the tiles 30. The UV reflective lamina 34 of the tiles will reflect this UV light to intensify UV radiation in the duct. Thus, air flowing through the duct will be exposed to the UV light which acts to purify the air.

Figure 5:
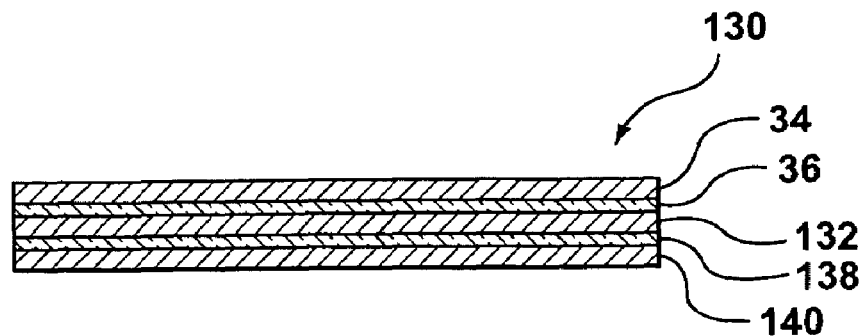
FIG. 5 is an enlarged cross-sectional view of a tile for use in the duct of FIG. 1 made in accordance with another aspect of the present invention.

FIG. 5 illustrates an tile alternative to tile 30. Turning to FIG. 5, tile 130 has a basal lamina 132 which may be a flexible sheet. A UV reflective lamina 34, such as an aluminum foil sheet, is adhered to the basal lamina by a layer 36 of adhesive. A layer 138 of pressure sensitive adhesive on the opposite side of the basal lamina 132 is covered by a release backing 140. In one embodiment, the basal lamina 132 and layers 36, 138 of adhesive may simply be a double-sided tape.

Installation of an air purifier in a duct using the tile 130 of FIG. 5 proceeds identically to installation using tile 30 of FIG. 4, except as follows. Prior to installation of a tile 130, the release backing 140 is removed from the tile exposing the layer 138 of pressure sensitive adhesive. Thereafter, the tile may be pressed against the interior surface of the duct so that the tile adheres to the duct. Optionally, prior to installing any of the tiles 130, the interior surface of the duct 10 where the air purifier will be installed may be cleaned. This will promote a stronger bond between adhesively mounted tiles and the duct.

As a further alternative to tile 30, a tile may be identical to tile 30 except that the basal lamina is a non-ferromagnetic flexible sheet. In such instance, a layer of adhesive may be painted on to the back of the basal lamina prior to installation, or fasteners may be used to attach the tile to the duct.

Figure 6:
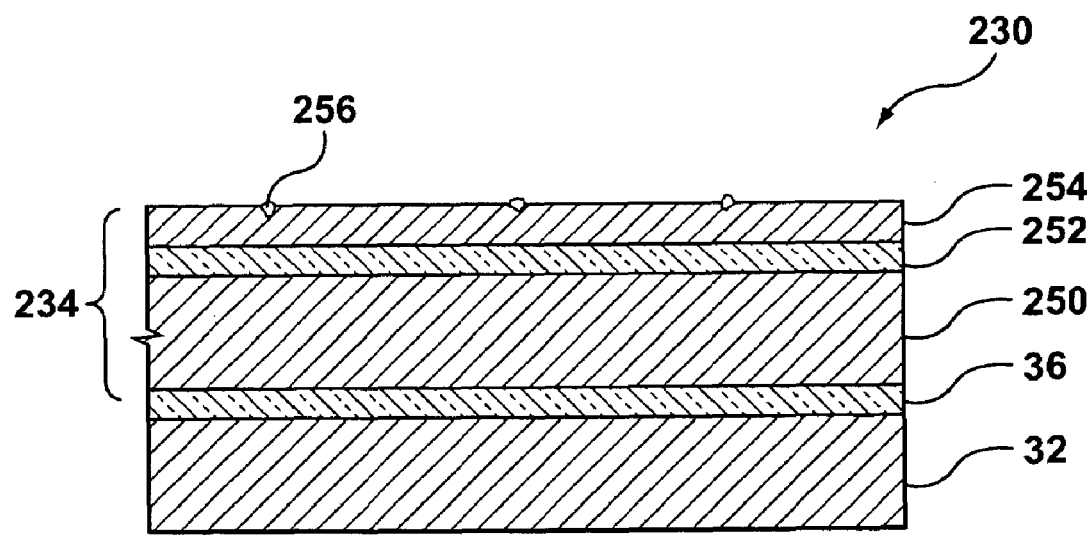
FIG. 6 is an enlarged cross-sectional view of a tile for use in the duct of FIG. 1 made in accordance with a further aspect of the present invention.

Flexible UV reflective lamina 34 of the tiles may be any suitable UV reflector. Thus, rather than being a reflective metal foil, the lamina 34 may comprise a substrate, such as paper, coated with a UV reflective paint. As a further option, the UV reflective lamina may provide a self-cleaning UV reflective surface. For example, turning to FIG. 6, tile 230 has a UV reflective lamina 234 comprising a substrate layer 250 (as, for example, paper, aluminum, or aluminized sheet) coated with a primer layer 252, which layer is then coated with a UV reflective paint layer 254. The UV reflective paint layer 254 has embedded in its upper surface nano-particles of a photo-catalytic semiconductor material, an exemplary nano-particle of which is indicated at 256.

The nano-particles 256 are dispersed over the surface of the UV reflective paint layer 254. These nano-particles 256 are composed of a photo-catalytic semiconductor material (as, for example, $TiO_2$) that leads to the production of oxygen and hydroxyl free radicals when illuminated with UV light in the presence of water vapor. Some of these free radicals oxidize surface films, converting the surface films into gaseous $H_2O$ and $CO_2$. This reduces the amount of the organic deposits on the surface of the reflective paint layer 254. For minimum catalytic activity, the semiconductor material is ideally highly UV absorbing.

The reflective paint layer 254 includes particles of a scattering material and a binding material. An exemplary composition consists of about 85 percent-by-weight barium sulfate 300 nm crystals and about 15 percent-by-weight of a 40 percent colloidal silica solution. These materials may be combined in a ball mill for 30 minutes of grinding. The components of the reflective paint layer 254 are chosen so that the reflective paint layer 254 is not reactive with the free radicals formed through the photo-catalytic action of the nano-particles 256. The scattering material used for the reflective paint layer 256 is selected for maximum scattering of incident optical energy. In choosing a suitable size for the particles (e.g., the 300 nm crystals), consideration must be given to a desired refractive index and the shape of the particles of scattering material. In general, the size for the particles will range from 20% to 200% of the wavelength of the light to be reflected. The binding material, colloidal silica in the above case, for the reflective paint layer 256 is selected for minimum absorbance at the wavelength to be reflected.

Preferably, the nano-particles 256 have a size that is less than one tenth of the UV wavelength to be reflected. For example, where the UV wavelength to be reflected is centered at 254 nm, a nano-particle size of about 25 nm is appropriate, for instance, Titandioxid P 25 from Degussa of Dusseldorf, Germany. This size makes the nano-particles 256 nearly invisible to the UV light. Smaller particles have a further advantage of being closer together than larger particles for the same percentage of surface coverage. This proximity benefits the self-cleaning process in that, in general, the distance the free radicals are required to travel is reduced. The self-cleaning action of the nano-particles 256 may be increased through the use of larger particles or a higher percentage coverage, however, these increases come at the cost of increased UV absorption. In practical terms, the size of particle is limited to a range of 0.5 nm to 1 000 nm while the percentage of coverage may range between 0.01% and 5.0%. Further details regarding such a self-cleaning UV reflective lamina are provided in aforereferenced U.S. Patent publication no. 20030059549.

As a further alternative tile, the UV reflective lamina could comprise a reflective metal foil to which nano-particles 256 are adhered by a thin, UV transparent glue.

As a further option, the basal lamina of the tiles and, optionally, the UV reflective lamina, is not flexible, but is instead rigid. This option is viable where the duct 10 in which the tiles will be installed has flat surfaces interior surfaces, as is the case for the duct 10 illustrated in FIG. 1. However, where the duct 10, instead of having the rectangular cross-sectional shape illustrated in FIG. 1, has a circular or irregular cross-sectional shape, the tiles may need to have flexible lamina so that the tiles may flex to conform to the interior shape of the duct.

Obviously, the tiles may be employed no matter what the orientation of the duct (horizontal or vertical).

One air purifier 12 has been installed, the purifier may be inspected by removing the panel 22 from the duct 10. If any of the tiles are found to be defective, or out-of-place, these tiles may readily be replaced.

It will be apparent that the air purifier 12 of this invention is particularly suited to fabrication from a kit wherein the components of the kit (tiles, UV light with supports, and ballast) are installed at an existing air duct.

Other modifications will be apparent to those skilled in the art and, therefore, the invention is defined in the claims.

What is claimed is:

1. A method of providing a UV reflective cavity, comprising:
   in a duct having a source of UV light, attaching a plurality of tiles, each having a UV reflective surface, to the interior surface of said ducts,
   wherein said attaching comprises magnetically adhering each of said plurality of tiles to said interior surface of said duct.

2. The method of claim 1 comprising cutting said plurality of tiles from a large sheet.

3. A method of providing a UV reflective cavity, comprising:
   in a duct having a source of UV light, attaching a plurality of tiles, each having a UV reflective surface, to the interior surface of said duct,
   wherein each of said plurality of tiles is flexible and further comprising conforming each of said plurality of tiles to a configuration of said interior surface of said duct during said attaching.

4. A method of providing a UV reflective cavity, comprising:
   in a duct having a source of UV light, attaching a plurality of tiles, each having a UV reflective surface, to the interior surface of said duct,
   wherein each tile comprises a UV reflective lamina adhered to a basal lamina and said basal lamina is a magnetic sheet.

5. The method of claim 4 wherein said UV reflective lamina is a metal foil.

6. The method of claim 4 wherein said UV reflective lamina comprises a substrate lamina coated with a UV reflective paint.

7. A method of providing a UV reflective cavity, comprising:
   in a duct having a source of UV light, attaching a plurality of tiles, each having a UV reflective surface, to the interior surface of said duct,
   wherein each tile comprises a UV reflective lamina adhered to a basal lamina and said basal lamina is an adhesive backed sheet.

8. The method of claim 7 wherein said adhesive backed sheet has a release backing releasably covering an adhesive layer.

9. The method of claim 8 wherein said adhesive layer comprises a pressure sensitive adhesive.

10. The method of claim 7 wherein said UV reflective lamina is a metal foil.

11. The method of claim 7 wherein said UV reflective lamina comprises a substrate lamina coated with a UV reflective paint.

12. An air purifier, comprising:
   an air duct;
   a plurality of tiles, each of said tiles having a UV reflective surface, adhered to the interior surface of said duct;
   a source of UV light for illuminating said tiles,
   wherein each tile comprises a UV reflective lamina adhered to a basal lamina and
   wherein said basal lamina is a magnetic sheet.

13. An air purifier, comprising:
   an air duct;
   a plurality of tiles, each of said tiles having a UV reflective surface, adhered to the interior surface of said duct;
   a source of UV light for illuminating said tiles,
   wherein each tile comprises a UV reflective lamina adhered to a basal lamina and
   wherein said basal lamina is an adhesive backed sheet.

14. The air purifier of claim 13 wherein said adhesive backed sheet has a release backing releasably covering an adhesive layer.

15. An air purifier, comprising:
   an air duct;
   a plurality of tiles, each of said tiles having a UV reflective surface, adhered to the interior surface of said duct;
   a source of UV light for illuminating said tiles,
   wherein each tile comprises a UV reflective lamina adhered to a basal lamina and
   wherein said basal lamina and said UV reflective lamina are flexible such that said tile is flexible.

* * * * *